(12) United States Patent
Lotzer et al.

(10) Patent No.: US 7,216,526 B2
(45) Date of Patent: May 15, 2007

(54) METHOD AND APPARATUS FOR MEASURING VANE WEAR IN A SLIDING VANE ROTARY PUMP

(75) Inventors: Michael R. Lotzer, Dousman, WI (US); Richard W. Plenkers, Watertown, WI (US); Mark A. Gaulke, Hartland, WI (US)

(73) Assignee: Rapco, Inc., Hartland, WI (US)

( * ) Notice: Subject to any disclaimer, the term of this patent is extended or adjusted under 35 U.S.C. 154(b) by 0 days.

(21) Appl. No.: 10/860,207

(22) Filed: Jun. 3, 2004

(65) Prior Publication Data

US 2005/0011248 A1    Jan. 20, 2005

Related U.S. Application Data

(60) Provisional application No. 60/475,290, filed on Jun. 3, 2003.

(51) Int. Cl.
*F01C 21/00* (2006.01)
(52) U.S. Cl. .................... 73/9; 418/2; 33/812
(58) Field of Classification Search ............... 418/2; 73/9; 33/812
See application file for complete search history.

(56) References Cited

U.S. PATENT DOCUMENTS

| | | |
|---|---|---|
| 706,158 A | 8/1902 | Charles |
| 2,781,000 A | 2/1957 | Thomas et al. |
| 3,191,852 A | 6/1965 | Kaatz et al. |
| 3,200,501 A * | 8/1965 | Keszler ............... 33/812 |
| 3,301,194 A | 1/1967 | Brunson |
| 3,398,884 A | 8/1968 | Kaatz et al. |
| 3,463,384 A | 8/1969 | Kilbane |
| 3,469,500 A | 9/1969 | Lutz et al. |
| 3,552,895 A | 1/1971 | Bayley |
| 3,565,558 A | 2/1971 | Tobacman |
| 4,804,317 A | 2/1989 | Smart et al. |
| 4,820,140 A | 4/1989 | Bishop |
| 5,318,409 A | 6/1994 | London et al. |
| 5,720,598 A | 2/1998 | de Chizzelle |
| 6,318,147 B1 | 11/2001 | Steinruck et al. |
| 6,368,066 B2 | 4/2002 | Aiyama et al. |
| 6,450,789 B1 | 9/2002 | Henderson |

(Continued)

FOREIGN PATENT DOCUMENTS

AU    82659/91    10/1991

OTHER PUBLICATIONS

Fruitland Tool and Mfg., Fruitland Vacuum Pump Operation and Maintenance Manual, Stoney Creek, ON, Canada.
Mannesmann-Demag, Instruction Manual and Spare Parts List for Air-Cooled Rotary Compressors and Vacuum Pumps, Nr. BE 10/1982/3US, 1982, Schopfheim, Germany, See p. 14.
Blackmer, Blackmer Rotary Vane Compressors Installation, Operation and Maintenance Instructions, Model: Model: E56, E106, E156, Oct. 1999, Grand Rapids, MI USA. See pp. 7-8.

(Continued)

*Primary Examiner*—Michael Cygan
(74) *Attorney, Agent, or Firm*—Quarles & Brady; Terri S. Flynn

(57) ABSTRACT

The amount of wear on the vanes of a sliding vane rotary pump is determined by inserting a wear inspection dip stick into a wear inspection port providing in a housing of the sliding vane rotary pump. The wear dipstick includes one or more mark providing an indication of the amount of wear on the vanes, and a marking member which provides an indication of current vane length and allows a maintenance person to easily determine when a pump replacement is required.

6 Claims, 4 Drawing Sheets

U.S. PATENT DOCUMENTS

| | | |
|---|---|---|
| 6,565,337 B2 | 5/2003 | Henderson |
| 6,769,886 B2 | 8/2004 | Henderson |
| 2002/0098099 A1 | 7/2002 | Henderson |
| 2002/0110467 A1 | 8/2002 | Henderson |
| 2003/0012671 A1 | 1/2003 | Henderson |

OTHER PUBLICATIONS

Lotzer, Michael, "Maximizing Vacuum Pump Life and Checking for Wear," Aviation Maintenance, Jun. 2002, Access Intelligence. (formerly PBI Media), Rockville, Maryland.

* cited by examiner

METHOD AND APPARATUS FOR MEASURING VANE WEAR IN A SLIDING VANE ROTARY PUMP

CROSS-REFERENCE TO RELATED APPLICATION

This application claims the benefit of provisional application Ser. No. 60/475,290, filed Jun. 3, 2003, hereby incorporated by reference.

STATEMENT REGARDING FEDERALLY SPONSORED RESEARCH OR DEVELOPMENT

Not applicable.

FIELD OF THE INVENTION

The present invention relates to dry air sliding vane rotary pumps, and more particularly to a method and apparatus for evaluating wear in the vanes without disassembling the pump housing.

BACKGROUND OF THE INVENTION

Sliding vane rotary pumps are well known for use in a variety of applications, and are particularly common in aeronautical and aviation applications. These devices are commonly used, for example, in powering gyroscopically controlled flight instruments in airplanes. Proper maintenance to prevent the failure of these devices is therefore very important.

Sliding vane rotary pumps typically comprise a rotor, a housing or stator, and a plurality of vanes. The rotor includes radial slots which receive the vanes, and can be constructed of either carbon, carbon composite, or hardened metal materials. The stator is typically constructed of a hardened metal material and the interior comprises an ellipsoidal cavity which receives the rotor. The vanes are typically constructed of carbon or carbon composites, and, as the rotor rotates, are caused by gravity to slide in and out of the slots as the rotor moves within the cavity, extending and retracting synchronously with the relative rotation of the rotor to provide compression and expansion of the air and therefore to produce a pumping pressure.

The sliding motion of the vanes, however, results in a significant degree of friction which is exacerbated by the atmospheric pressures induced when used in aviation applications. While a number of efforts have been made to mitigate the frictional wear from the sliding vanes, including, for example, employing various coatings on both the vanes and the rotor, wear and breakage of the vanes remains problematic, as the friction developed between the vane and the rotor is eventually destructive to the pump. As the vanes reciprocate in the rotor slots, friction causes the vanes to wear, eventually shortening the vanes until they no longer reciprocate in the slots properly. Eventually, the shortened vanes lead to pump failure. Although the wear on the vanes can be monitored to some extent on the aircraft's vacuum gauge, which provides an indication if the pump is not operating correctly, there is generally little warning of a pending failure, as pump performance and efficiency are generally unaffected by wear on the vanes until a total or near total failure occurs.

To prevent such failures, the operation time of the pump is monitored and the number of hours of operation is used as a benchmark for determining when to replace the pump. While generally effective in preventing pump failure, replacing the pump based entirely on hours of operation is expensive, resulting in premature pump replacement even when no significant wear has occurred, and further incurring costs in the form of maintenance time, down time for the vehicle and equipment expense. To reduce the equipment costs, the pump can be removed from the equipment and disassembled to evaluate the amount of wear. Again, however, this operation requires a high degree of maintenance activity, significant vehicle down time, and is highly dependent on the opinion of the evaluator.

Another alternative, in which the length of the vanes are visually monitored, has been proposed in U.S. Pat. No. 6,450,789. Here, a "view port" is provided in a back of the housing of the pump. Through the view port, a maintenance person can examine the length of the vanes with reference to the width of the port and/or an associated calibration hole. While providing a means for viewing the rear on the vane, the view port can be difficult to access in the vehicle, and further requires a judgment call on the part of the maintenance personnel examining the pump.

There remains a need, therefore, for an easy, consistent and effective way to gauge the wear on a vane in a dry air sliding vane pump without requiring removal or disassembly of the pump.

BRIEF SUMMARY OF THE INVENTION

One object of the invention is to provide a dipstick for determining wear on a vane in a sliding vane rotary pump. The dipstick comprises an elongated member, sized and dimensioned for insertion into an inspection port provided in a side of the sliding vane rotary pump which selectively provides access to at least one vane in the pump. A wear indicator mark is located on the elongated member in a position selected to indicate that the sliding vane rotary pump is worn when the elongated member is inserted into the inspection port. A marking device is slideably mounted on the elongated member, wherein when the elongated member is inserted into the inspection port, the marking device is slidable along the elongated member to contact the housing. In this position, the marking device provides a comparator for visually comparing the wear of the vane to the wear indicator mark.

Another object of the invention is to provide a sliding vane rotary pump and a wear calibration device, in combination. The wear calibration device comprises an elongated wear calibration member including a wear indicator mark, and a marking device is slideably mounted on the elongated wear calibration member. The rotary vane pump comprises a housing including an inspection port, wherein the interior of the housing defining a bore for receiving a rotor. The rotor includes a plurality of radially-extending slots, and a plurality of vanes corresponding to the plurality of slots in the rotor are slideably received in the slots. To check the wear on the vanes, the elongated member is inserted into the inspection port when the slots in the rotor are selectively aligned with the inspection port, until the elongated member contacts a vane. The marking member is slid to a position contacting the outer surface of the housing to provide a mark which is then comparable to the wear indicator mark on the elongated member to indicate an amount of wear on the vane.

Another object of the invention is to provide a method for determining the amount of wear on a vane in a sliding vane rotary pump including a housing defining an interior wall, a rotor provided within the interior wall and comprising a plurality of radially-extending slots, and a plurality of vanes, the number of vanes corresponding to the number of slots. The method comprises providing an inspection port in the housing of the sliding vane rotary pump to provide access to the slots in the rotor, calibrating an elongated member sized and dimensioned to be insertable in the inspection port to include a calibration mark indicating a length at which the vanes are worn and the pump should be replaced, rotating the rotor until the inspection port aligns with a slot in the rotor, and inserting the elongated member into the inspection port until it contacts the vane in the rotor. After the elongated member is inserted into the inspection port, the insertion length is compared versus the calibrated wear indicator mark to determine whether to replace the pump.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE INVENTION

Figure 1:
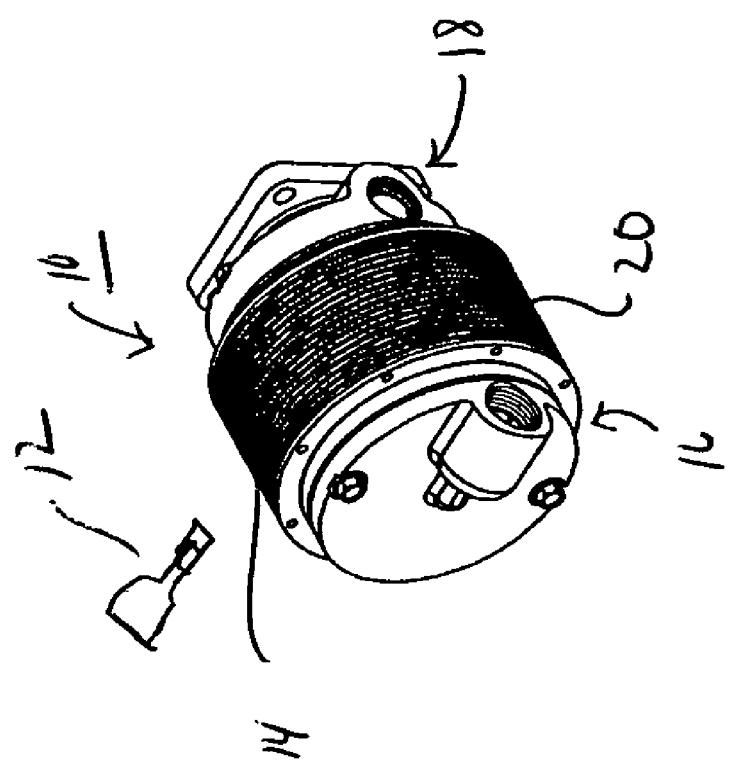
FIG. 1 is a perspective view of a sliding vane rotary pump.

Referring now to the figures and more particularly to FIG. 1, a sliding vane rotary vacuum pump 10 is shown. The vacuum pump 10 comprises a housing 20 including an inspection port 14 for receiving a wear inspection dipstick 12. The housing 20 is enclosed by a rear end 16 and front end 18 each of which includes a threaded aperture for receiving a pipe (not shown) for circulating air through the pump 10.

Figure 2:
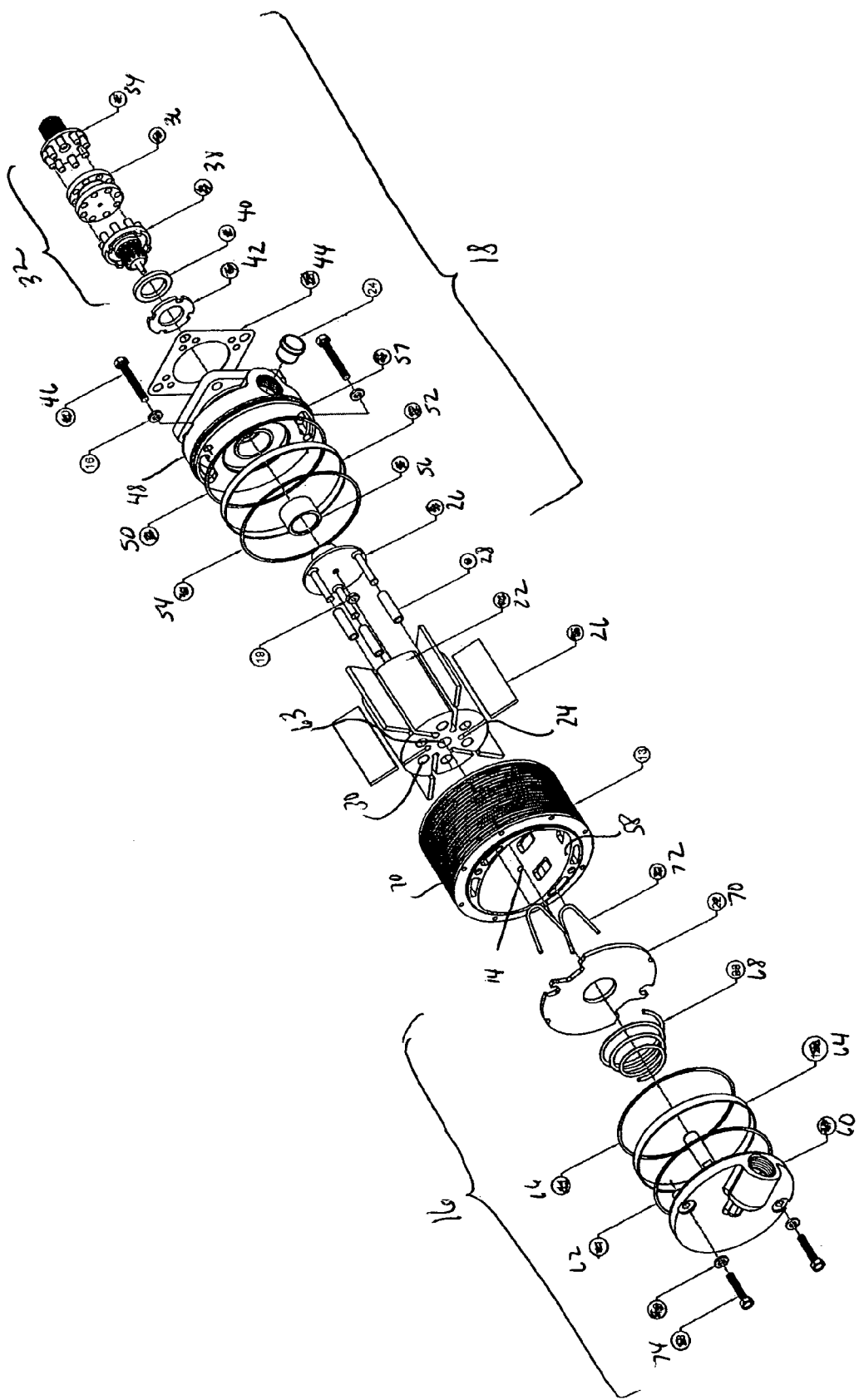
FIG. 2 is an exploded view of the sliding vane rotary pump of FIG. 1.

Referring now to FIG. 2 an exploded view of the vacuum pump 10 of FIG. 1 is shown. The housing 20 comprises an ellipsoidal pump cavity 58 which receives a rotor 22 comprising a plurality of slots 24 extending radially inward towards the center of the rotor from the outer edge of the rotor 22. Each of the slots 24 receives a rotary vane 26 which is slidably engaged in the corresponding slot 24. The rotor 22 further comprises a plurality of apertures extending longitudinally through the rotor 22 for receiving the fingers of a three-finger drive 26 and a central aperture 63 for receiving a central cylindrical member 61 in the rear end plate 60, as described below. Each of the fingers of the three finger drive 26 is associated with a cushion 28, the cushions 28 being provided between the apertures 30 and the drive 26 minimizing wear of the rotor 22.

Referring still to FIG. 2, as described above, the three-fingered drive 26 is coupled at a first end to the rotor 22. At the opposing end, the three-fingered drive 26 is coupled to a drive shaft 32 comprising an external spline 34, a shear shaft 36, and an internal spline 38. The external spline 34 can be coupled to an external drive mechanism for rotating the drive shift 32, the three-fingered drive 26, and therefore to rotate the rotor 22. The drive shaft 32 extends outside of a front end mounting plate 48 which is coupled to the internal spline 38 of the drive shift 32 through a gasket 44, a ceramic drive plate 42, and a sponge 40. The front end mounting plate 48 is further coupled to the housing 20 of the pump 10 through first and second rubber seals 50 and 54 and a metal ring 52.

At the opposing end of the pump 10, the housing 20 is enclosed by the rear end 16. The rear end 16 includes a rear end plate 60 which is coupled to the housing 20 with first and second rubber seals 62 and 66 and a metal ring 64. A clockwise/counterclockwise adaptor plate 70, selectively activated to reverse the direction of air flow from clockwise to counterclockwise, is also coupled to the housing 20 via retainer clips 72. A spring 68 is provided between the clockwise/counterclockwise adaptor plate 70 and the rear end plate 60. The rear end plate 60 further comprises a central cylindrical member 61 extending from the center of the rear end plate toward the rotor 22 which is received in the central aperture 63 in the rotor 22, as described above.

Referring still to FIG. 2, in operation an external drive system is coupled to the drive shaft 32 of the front end 18 of the housing 20. As described above, the external drive system drives the drive shaft 32 which causes the three-finger drive 26 to rotate in the rotor 22, thereby rotating the rotor 22 within the ellipsoidal pump cavity 58. As the rotor 22 rotates within the ellipsoidal cavity 58 the vanes 26 are forced by centrifugal forces to slide into and out of the slots 24 when rotated. As the vanes 26 slide in and out of the rotor 22, air is compressed in the pump cavity 58 such that a pump pressure develops as is known in the art and is described, for example, in U.S. Pat. Nos. 6,450,789 B1; 4820,140; 3,191,852; and 4,804,317, each of which describe a sliding vane rotary device and which are incorporated herein by reference for their description of such devices.

Figure 3:
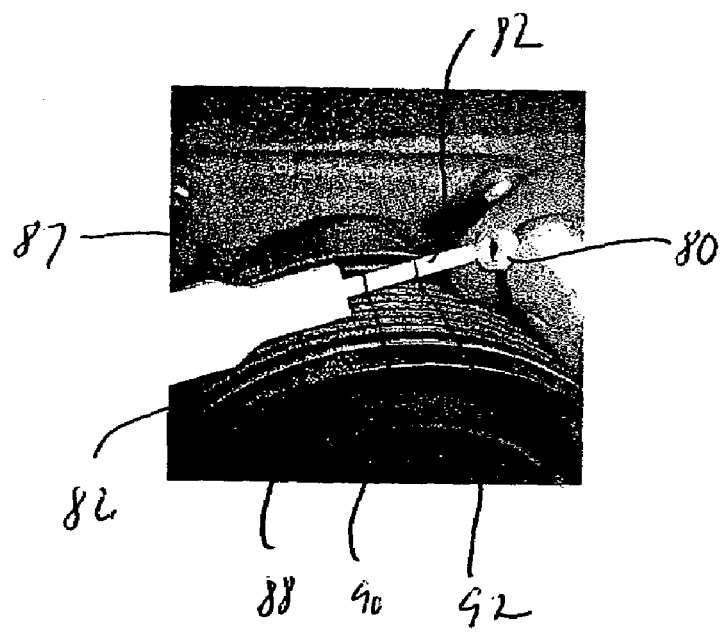
FIG. 3 is a perspective view of a wear inspection dipstick.

Referring now to FIG. 3, the wear inspection dipstick 12 comprises an elongated member 82 extending from a handle portion 84. The handle portion 84 comprises a wide handle section 86 which is sized and dimensioned to allow for easy handling by an operator, and a mounting section 88 coupled to the handle section 86 through a tapered section 87. The elongated member 82 extends from a central portion of the mounting section 88 and includes first and second wear indicator marks 90 and 92, respectively, which are located on the elongated member 82 to provide a visual comparison point when testing the wear of the vanes 26 in the pump 10. The elongated member 82 is in turn sized and dimensioned to extend into the wear inspection port 14 in the housing 20 of the vacuum pump 10.

Referring still to FIG. 3, a marking member, here shown as a collar 80, is sized and dimensioned to be slidably received on the elongated member 82, and is provided to "mark" wear on the wear inspection dipstick 12 in use. As shown, the collar 80 is preferably ring-shaped, the inner diameter being selected to be slidably received on the elongated member 82, and the outer diameter selected to be greater than the outer diameter of the inspection port 14 in the housing 20, such that the collar 80 is stopped consistently when it is slid into the housing 20, thereby consistently marking a position on the elongated member 82.

Figure 4:
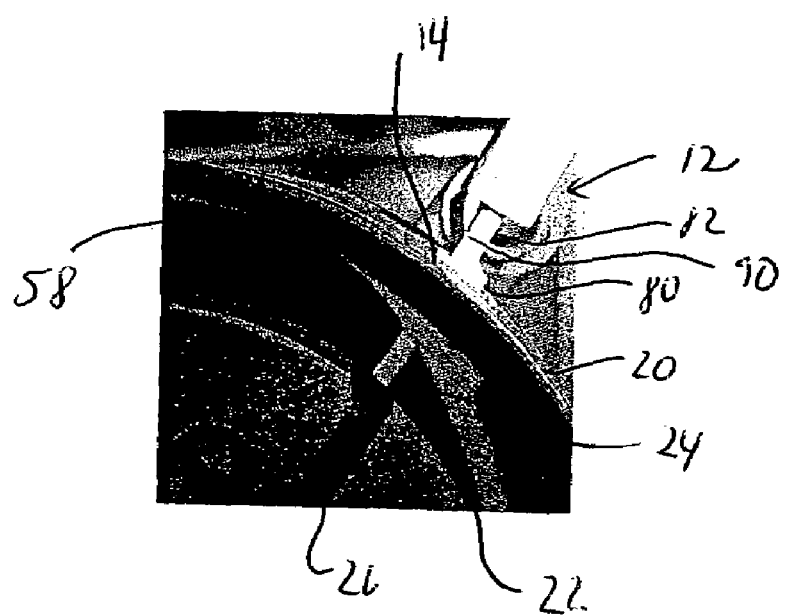
FIG. 4 is a cutaway view of the pump of FIG. 1, illustrating the insertion of the dipstick of FIG. 2 in the wear inspection port.

Referring now to FIG. 4, in use a cap (not shown) is removed from the wear inspection port 14 when the magnetos used to ignite the engine are turned off. The rotor 72 is rotated, typically by rotating a propeller coupled to the vacuum pump 10, until the wear inspection port 14 is aligned with a slot 24 in the rotor 22. The wear inspection port 14 is located in the housing 20 and extends through the pump cavity 58 through the ellipsoidal interior wall. The alignment of the wear inspection port 14 and the slot 24 can be checked, for example, by shining a flashlight in the inspection port 14 and visually gauging the alignment. As can be seen from FIG. 4, the inspection port 14 is preferably positioned at the upper portion of the pump such that the vane 26 in the slot 24 located adjacent the wear inspection port 14 is forced by gravity into the slot 24. In this position, the length of the vane 26 can be determined as a function of the distance between the top end of the vane 26 and the housing 20 through the wear inspection port 14.

When the wear inspection port 14 is aligned with the slot 24, the collar 80 is slid onto the elongated member 82 and the wear inspection dipstick 12 is inserted into the wear inspection port 14. The collar 80 is slid into contact with the housing 20, wherein the collar 80 provides a mark indicating the distance that the elongated member 82 was inserted into the wear inspection port 14. The collar 80, therefore, provides a measure of the length of the vane 26, as a function of its position on the elongated member 82, and the position of the collar 80 can be compared against the positions of the wear marks 92 and 94 to determine the amount of wear on the vanes 26.

Figure 7:
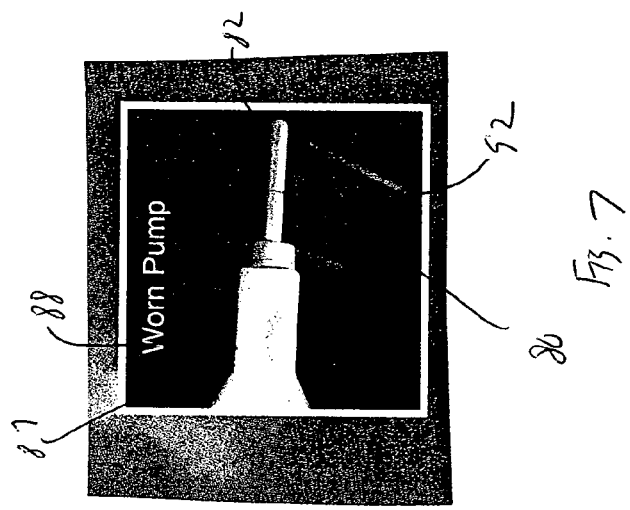
FIG. 7 is a perspective view of the dipstick illustrating a worn pump.
Figure 6:
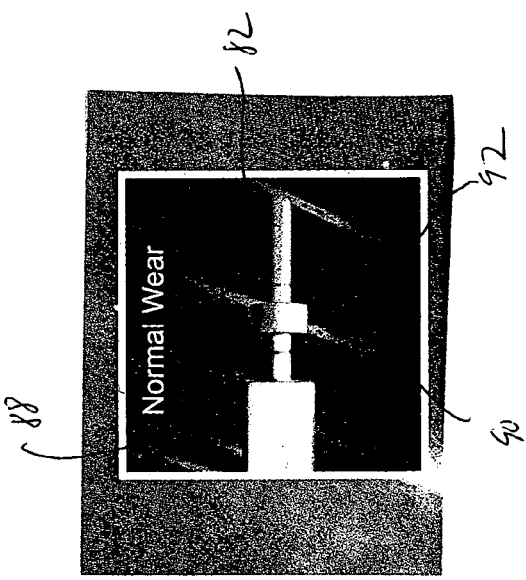
FIG. 6 is a perspective view of the dipstick illustrating normal pump wear.
Figure 5:
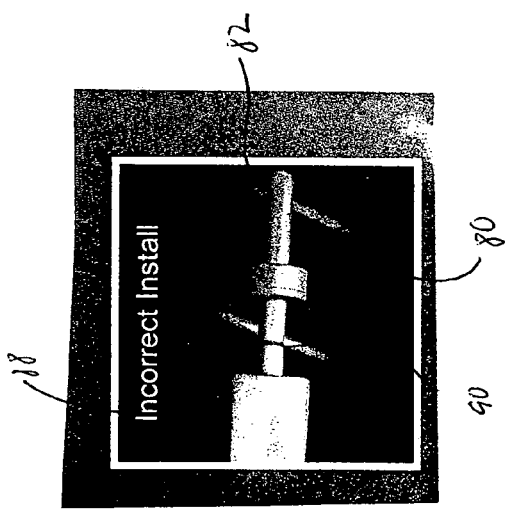
FIG. 5 is a perspective view of the dipstick illustrating an incorrect installation.

Referring now to FIGS. 5–7, the position of the collar 80 on the wear inspection dipstick 12 is shown in three wear measurement situations. In FIG. 5 the collar 80 is shown at the wear indicator mark 92 which is located on the elongated member 82 to indicate that the elongated member 82 has contacted the outer surface of the rotor 22 rather than the slot 24. Therefore, the mark 92 indicates that the wear inspection port 14 is not aligned with the slot 24 in the rotor 20. In FIG. 6 the collar 80 is shown marking a position between the wear marks 90 and 92. This position indicates that the wear of the vanes 26 in pump 10 is normal and that the pump need not be replaced at this time.

Referring now to FIG. 7, here the collar 80 is positioned over the wear indicator mark 90. When the collar 80 appears in this position the length of the vane 26 is less than desirable, indicating significant wear. Therefore, the pump 10 needs to be replaced.

In alternative embodiments, a wear indicator port 14 could be provided in alternate locations in the housing 20. For example, a wear indicator port 14 could be provided in an end of the housing 20, such as in the rear end plate 60. Here, the dipstick 12 is not be calibrated to check the distance to the vane 26 from the housing 20, as described above. Rather, the position of the wear indicator port 14 is selected to be positioned at a location in which, when the dipstick 12 is inserted, the absence of a vane 26 indicates that the pump needs to be replaced, and the presence of the vane 26 indicates that the vane 26 has not worn to the point at which it needs to be replaced. Appropriate wear marks, positioned on the elongated member 82 as described as described above, would be included to provide a comparator for visualizing the results of the inspection. Other alternative embodiments, in which, for example, the wear inspection port is provided on the front mounting plate 48, or positioned in a bottom portion of the housing 20 wherein the vanes 26 are slid out of the rotor, and the position is verified by inspecting the position of the back end of the vane 26 as opposed to the tip end, are also possible.

It should be understood that the methods and apparatuses described above are only exemplary and do not limit the scope of the invention, and that various modifications could be made by those skilled in the art that would fall under the scope of the invention. For example, although a specific embodiment of a sliding vane rotary pump has been shown and described, it will be apparent that the method and apparatus for determining wear in the vanes described above could be used in a number of similar devices, including those described in the patents incorporated by reference above. Furthermore, although a specific ring-shaped collar 80 has been described for marking the wear on the dipstick 12, it will be apparent that a number of different sliding or moving markers could also be used. Additionally, although a specific dipstick configuration and associated handle has been described, various other handle and member configurations could also be employed. To apprise the public of the scope of this invention, therefore, the following claims are made:

We claim:

1. In combination, a sliding vane rotary pump and a wear calibration device, comprising:
    a housing, the interior of the housing defining a bore;
    an inspection port formed in the housing;
    a rotor including a plurality of radially-extending slots, the rotor being positioned within the bore; and
    a plurality of vanes corresponding to the plurality of slots in the rotor, each of the vanes being slideably received in a corresponding slot;
    an elongated wear calibration member including a first indicator mark at a position pre-calibrated to indicate that the wear calibration member is in contact with the rotor and therefore incorrectly inserted when inserted into the inspection port and a second indicator mark at a position from the end of the member pre-calibrated to indicate that the pump is worn and should be replaced when inserted into the inspection port; and
    a marking device slideably mounted on the elongated wear calibration member to provide a comparator to the first and second indicator marks;
    wherein the elongated member is inserted into the inspection port until the elongated member contacts a surface and the marking device is slid along the elongated member until the marking device contacts the housing to provide a mark comparable to the first and second indicator marks to indicate whether the elongated wear calibration member is inserted in a slot and whether the pump is worn.

2. The combination as defined in claim 1, wherein the marking device is a ring-shaped collar.

3. The combination as defined in claim 2, wherein the inner diameter of the ring is sized and dimensioned to be slideably received on the elongated member.

4. The combination as defined in claim 2, wherein the outer diameter is sized and dimensioned to be greater than the outer dimension of the inspection port.

5. The combination as defined in claim 1, wherein the inspection port is located on an upper portion of the housing, wherein when the rotor is located adjacent the inspection port, the vanes are slid into the slots in the rotor.

6. The combination as defined in claim 1, wherein the portion of the elongated calibration member between the first indicator mark and the second indicator mark indicates normal wear.

* * * * *